United States Patent [19]

Drent

[11] Patent Number: 4,731,487

[45] Date of Patent: Mar. 15, 1988

[54] PROCESS FOR THE PREPARATION OF ALDEHYDES

[75] Inventor: Eit Drent, Amsterdam, Netherlands

[73] Assignee: Shell Oil Company, Houston, Tex.

[21] Appl. No.: 918,243

[22] Filed: Oct. 14, 1986

[30] Foreign Application Priority Data

Oct. 29, 1985 [GB] United Kingdom ............... 8526613

[51] Int. Cl.$^4$ ............................................. C07C 45/50
[52] U.S. Cl. .................................................. 568/454
[58] Field of Search ............................... 568/454, 450

[56] References Cited

U.S. PATENT DOCUMENTS

| | | | |
|---|---|---|---|
| 3,876,672 | 4/1975 | Mrowca | 568/454 |
| 4,215,077 | 7/1980 | Matsumoto et al. | 568/454 |
| 4,224,255 | 9/1980 | Smith | 568/451 |
| 4,317,936 | 3/1982 | Kim et al. | 568/454 |
| 4,370,258 | 1/1983 | Ogata et al. | 430/429 R |
| 4,390,729 | 6/1983 | Oswald | 568/454 |
| 4,424,380 | 1/1984 | Hsu | 568/454 |
| 4,467,116 | 8/1984 | van Leeuwen et al. | 568/454 |
| 4,564,711 | 1/1986 | Hsu et al. | 568/454 |
| 4,575,564 | 3/1986 | Hsu | 568/454 |

FOREIGN PATENT DOCUMENTS 0121965 10/1984 European Pat. Off. ............ 568/433

OTHER PUBLICATIONS

"Hydroformylation of 1-Hexene Catalysed by Complexes of Rhodium(1) with DI- or Tritertiary Phosphines", Alan R. Sanger, *J. of Molecular Catalysis*, vol. 3 (1977/78), pp. 221-226.

"The Structures and Hydroformylation Catalytic Activities of Polyphosphine Complexes of Rhodium(I), and Related Complexes Immobilised on Polymer Supports", Sanger et al, *J. of Molecular Catalysis*, vol. 3 (1977/78), pp. 101-109.

*Primary Examiner*—Werren B. Lone

[57] ABSTRACT

Process for the preparation of aldehydes by hydroformylation of an alkenically unsaturated compound in the presence of (a) Pd, a Pd compound, Pt and/or a Pt compound, (b) an anion of a carboxylic acid with a $pK_a < 2$, and (c) a bidentate ligand $R^1R^2$-M-R-M-$R^3R^4$, wherein M is P, As or Sb, R is a divalent organic bridging group having at least 3 carbon atoms in the bridge, and $R^1$, $R^2$, $R^3$ and $R^4$ are hydrocarbon groups.

16 Claims, No Drawings

PROCESS FOR THE PREPARATION OF ALDEHYDES

FIELD OF THE INVENTION

The invention relates to a process for the preparation of aldehydes by hydroformylation of an ethylenically unsaturated compound having at least five carbon atoms per molecule.

BACKGROUND OF THE INVENTION

The hydroformylation of ethylenically unsaturated compounds, i.e. the catalytic addition of carbon monoxide and hydrogen to such compounds to produce aldehydes and/or alcohols is of great industrial importance. Aldehydes, in particular linear (i.e., straight-chain) aldehydes, are very useful intermediates in industrial practice because of their terminal carbonyl group. They can, for instance, be readily reduced to the corresponding primary alcohols and oxidized to the corresponding carboxylic acids. The aldehydes also undergo addition and/or condensation reactions with a variety of chemicals such as hydrogen cyanide, alcohols, nitroparaffins as well as condensation reactions with themselves and other carbonyl-containing compounds. They can also be reacted with ammonia and derivatives thereof such as primary amines.

Much effort has been devoted over the years to the development of better catalytic systems for hydroformylation reactions, especially with the objective to improve the ratio of linear to branched molcules in a product prepared from a linear starting material. Linearity of the carbon chain in the product molecule has a positive influence on properties such as biodegradability, which is of great importance in various applications wherein aldehydes and/or alcohols are used as intermediates or starting materials, and particularly in application wherein the hydroformylation product is used in the preparation of surfactant compounds.

Since it is known that the classical cobalt carbonyl catalyst system for hydroformylation produces a large amount of branched chain products, more advanced systems have been suggested comprising organophosphorus compounds, in particular tertiary phosphines or phosphites as ligands.

Not only ligands have been suggested as promoters and/or stabilizers for hydroformylation catalysts but also certain metal halides are recognized for this service. For instance, it is known that Group IVA metal halides, in particular tin(II)-halides, preferably also containing a quarternary ammonium halide, can also be applied to improve the linear/branched product ratio, especially when platinum is used as the main catalyst.

However, the use of Group IVA halides has the intrinsic drawback that normally a rather large excess of such compound is required which, makes the work-up procedure for recovery of product and recovery and recycle of starting material and catalyst very unattractive. Moreover, it appears that high linear/branched product ratios can only be obtained at the expense of an increasing amount of alkanes being co-produced. It is therefore very desirable to develop a hydroformylation catalyst, which matches the activity (e.g., reaction rate) of the cobalt-carbonyl based catalyst, while maintaining a high linear/branched product ratio with a minimal coproduction of undesired alkanes.

SUMMARY OF THE INVENTION

It has now been found that ethylenically unsaturated compounds can selectively be hydroformylated to aldehydes at acceptable rate with a very low amount of alkanes being co-produced even at high product molecule linearity when the process is carried out in the presence of a specific ligand stabilized catalytic system.

Accordingly, the present invention provides a process for the preparation of aldehydes by hydroformylation of an alkenically unsaturated compound having at least 5 carbon atoms per molecule, which comprises contacting the alkenically unsaturated compound with carbon monoxide and hydrogen in the presence of an aprotic solvent and a catalytic system which comprises a. one or more catalysts selected from the group consisting of palladium, palladium compounds, platinum, platinum compounds, and mixtures thereof, b. one or more anions of one or more carboxylic acids having a $pK_a < 2$, measured in aqueous solution at 18° C., and c. one or more bidentate ligands of the general formula

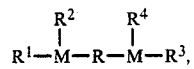

wherein M represents phosphorus, arsenic or antimony, R represents a divalent organic bridging group having at least three carbon atoms in the bridge, and $R^1$, $R^2$, $R^3$ and $R^4$ are the same or different hydrocarbon groups.

DESCRIPTION OF THE PREFERRED EMBODIMENTS

The invention is applicable to the hydroformylation of alkenically unsaturated hydrocarbons containing 5–30, preferably 5–12, carbon atoms per molecule. Most preferably the starting material is one or more alkenes or cycloalkenes. Examples of suitable alkenes include the isomeric pentenes, hexenes, octenes and dodecenes, cyclooctene and cyclododecene. Examples of other alkenically unsaturated compounds are styrene, α-methylstyrene, acrylic acid, methacrylic acid, alkyl esters of these acids and dialkenes in which the two unsaturated groups are not conjugated. In one aspect of the invention, the use of an alkenically unsaturated hydrocarbon starting material having a linear structure in a major portion of the molecules is preferred from the standpoint of producing valuable linear aldehyde products. More preferably, the unsaturated reactant is comprised of at least about 70% linear molecules.

The catalyst component selected from the group consisting of palladium, platinum, palladium compounds and platinum compounds, is very preferably one selected from the group consisting of palladium and palladium compounds. Palladium compounds are considered mort preferred and it is with reference to palladium compounds that hereinafter the process according to the invention is described in greatest detail.

Both homogeneous and heterogeneous palladium compounds can be used. Homogeneous systems are preferred. Examples of suitable palladium compounds include salts of palladium with nitric acid, sulfuric acid or alkanoic acids containing not more than 12 carbon atoms per molecule. Salts of hydrohalogenic acids can in principle be used as well, but they have the drawback that the halogen ion may produce corrosion. Palladium carboxylates are the preferred catalyst compounds, in particular palladium acetate. Further, palladium acetylacetonate is also suitable. Palladium metal supported on carbon, and palladium combined with an ion exchanger are examples of suitable heterogeneous palladium catalysts.

The quantity of palladium, palladium compound, platinum and/or platinum compound applied in the process of this invention is not critical. Preference is given to the use of quantities in the range of from $10^{-8}$ to $10^{-1}$ mole of palladium, palladium compound, platinum and/or platinum compound per mol of alkenically unsaturated compound to be hydroformylated. The molar ratio of alkenically unsaturated hydrocarbon to carbon monoxide reactant will generally range from 5:95 to 95:5, preferably from 1:5 to 5:1.

Suitable carboxylic acids for use as the second component of the catalyst system for the invention are trichloroacetic acid, trifluoroacetic acid, dichloroacetic acid and difluoroacetic acid. The use of trifluoroacetic acid is considered most preferred. The acid necessarily has a pKa of less than 2, measured in aqueous solution at 18° C.

Preferably the anion of this carboxylic acid component is present in the reaction mixture in a quantity of 0.01-150, in particular 0.1-100 and most preferably 1-50, equivalents per gram atom palladium and/or platinum. The best results are usually obtained when at least 5 equivalents are present.

The one or more bidentate ligands which form the third component of the catalytic system of the invention are ligands capable of the formation of complex compounds of the formula

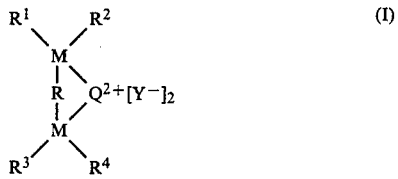

In formula (I), Q represents Pt or Pd, Y represents a non-coordinating anion, while $Q^{2+}$ can also be written as

in which the ligands $L_1$ and $L_2$ are weakly coordinated solvent ligands, e.g. acetonitrile, methanol, acetone, or acetylacetone, or correspond with those contained in the suitable palladium compounds described above. M may be phosphorus, arsenic, or antimony, but preferably represents phosphorus.

Hydrocarbon groups $R^1$, $R^2$, $R^3$ and $R^4$ will as a rule contain 2 to 18 carbon atoms, preferably 6 to 14 carbon atoms. Aryl groups are the most suitable, in particular the phenyl group or substituted, preferably hydrocarbon-substituted, phenyl groups. The hydrocarbon groups $R^1$, $R^2$, $R^3$ and $R^4$ may be the same or different and each may optionally carry one or more nonhydrocarbon substituents which do not interfere with the process. Preferred bridging groups —R— are those having the formula $(CR^5R^6)$ in which $R^5$ and $R^6$ are hydrogen atoms or hydrocarbon groups offering no steric hindrance and n is 3 or 4. Substituents $R^5$ and $R^6$ are preferably hydrogen atoms. The bridging groups R may also be part of cyclic structure, e.g. an aromatic or cycloaliphatic group, the carbon to carbon bond or bonds in the bridge may be saturated or unsaturated and in the bridge or in the cyclic or non-cyclic groups attached to the bridge one or more hetero atoms, e.g. sulfur, oxygen, iron or nitrogen, may have been substituted for carbon atoms, other than the two carbon atoms which must be present in the bridge linking both atoms M.

The bidentate ligands must have a molecular structure which is free of substituents which would sterically hinder formation of complexes of formula (I).

Examples of suitable bidentate ligands are
1,3-di(diphenylphosphino)propane,
1,4-di(diphenylphosphino)butane,
2,3-dimethyl-1,4-di(diphenylphosphino)butane,
1,4-di(dicyclohexylphosphino)butane,
1,3-di(di-p-tolylphosphino)propane,
1,4-di(di-p-methoxyphenylphosphino)butane,
2,3-di(diphenylphosphino)-2-butene,
1,3-di(diphenylphosphino)-2-oxopropane,
2-methyl-2-(methyldiphenylphosphino)-1,3-di(diphenylphosphino)propane,
0,0'-di(diphenylphosphino)biphenyl,
1,2-di(diphenylphosphino)benzene,
2,3-di(diphenylphosphino)naphthalene,
1,2-di(diphenylphosphino)cyclohexane,
2,2-dimethyl-4,5-di(diphenylphosphino)dioxolane
and

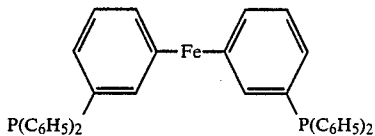

It is observed that compounds having a structure such as that of 2-methyl-2-(methyldiphenylphosphino)-1,3-di(diphenylphosphino)-propane, $CH_3-C-(CH_2-P(C_6H_5)_2)_3$, although being trifunctional, are nevertheless considered bidentate ligands in the terms of this invention since only two of the three phosphorus atoms are capable of coordinating with the palladium or platinum atom in complex (I).

The bidentate ligand can be employed in quantities which may vary within wide limits, e.g. of from 0.1 to 10 mol per mol of palladium, palladium compound, platinum and/or platinum compound component. Preferred quantities lie between 0.33 and 5 mol per mol.

The hydroformylation according to the invention is preferably carried out at a temperature between about 20° and 200° C., in particular between about 50° and 150° C. The overall pressure preferably lies between about 1 and 100, in particular between about 20 and 75, bar above atmospheric pressure.

The process according to the present invention can be carried out suitably using a molar ratio of carbon monoxide to hydrogen of 1:1 which is the stoichiometric ratio to produce aldehydes. Excess carbon monoxide or hydrogen over the stoichiometric amount may be present, however, for instance in a molar ratio between about 12:1 and 1:12. Good results have been obtained using a carbon monoxide:hydrogen ratio of about 1:1.

The process according to the present invention is carried out in the presence of an aprotic solvent. A variety of reaction solvents can be applied such as ketones, e.g. acetone, methyl ethyl ketone, methyl isobutyl ketone, acetophenone and cyclohexanone; ethers, such as the dimethylether to diethylene glycol (also referred to as "diglyme"), anisole, diphenyl ether; aromatic compounds, such as benzene, toluene and the three xylenes; halogenated aromatic compounds, such as chlorobenzene and ortho-dichlorobenzene; halogenated paraffinic hydrocarbons, such as methylene chloride and carbontetrachloride; paraffins such as hexane, heptane, cyclohexane, methylcyclohexane and iso-octane; nitriles, such as benzonitrile and acetonitrile and esters such as methyl benzoate. Good results have been obtained using methyl benzoate. Also mixtures of solvents can be suitably applied. It is also possible to use an excess of the starting material as well as of one or more of the appropriate ligands as solvent(s).

The contact of the alkenically unsaturated starting material with carbon monoxide and hydrogen, in the presence of the aprotic solvent and the specified catalytic system yields the corresponding aldehyde. If desired, the aldehyde product can then subjected to a catalytic hydrogenation, e.g. over a Raney-Ni catalyst to convert part of all of the aldehyde into the corresponding alcohol. The reaction conditions to be applied for preparation of the alcohol are well known in the art.

The process according to the present invention can be readily carried out using well-known chemical engineering practice which includes continuous, semi-continuous and batch operation. The reaction time may vary between wide limits, from a couple of minutes to several hours depending on the specific alkenically unsaturated compound and catalytic system applied. After the reaction the reaction mixture is suitably worked up by techniques known in the art. The product aldehyde can be removed by various means, e.g. by distillation. It is also possible to recycle part or all of the reaction mixture together with the catalytic system.

The following Examples further illustrate certain preferred aspects of the invention, but are not intended to limit its broader scope.

EXAMPLES 1-11 AND COMPARATIVE EXPERIMENTS A-G

A series of experiments were carried out in a 300 ml-Hastelloy C autoclave ("Hastelloy" is a trade name). The autoclave was charged with octene starting material, a solvent (30 ml), a palladium, platinum or ruthenium compound, a ligand and an acid. Table I hereinafter shows which components and how much thereof was used in each experiment. In Table I "$p$" denotes a phenyl group, "Acac" denotes "acetylacetonate" and "pTsA" denotes p-toluenesulfonic acid. The "i-octenes" consisted of 2.5% mol 1-octene, 39% mol 2-octene, 39% mol 3-octene and 19.5% mol 4-octene.

The autoclave was then pressurized with an equimolar mixture of carbon monoxide and hydrogen until an initial pressure of 68 bar was reached. The temperature was raised to a value indicated in Table I and the reaction mixture was kept at this temperature for the time stated in the Table. The reaction mixture was then allowed to cool and was analysed thereafter using gas-liquid chromatography. The results are presented in Table II. The "selectivity to nonanals", expressed in a percentage, is defined as $100 \times a/b$, in which "a" is the amount of nonanals in the product and "b" is the sum of the amounts of nonanals, nonanols and nonanes in the product. The "linearity of nonanals" is defined as the percentage of n-nonanal among the nonanals. The "selectivity to alkanes", express in a percentage, is defined as $100 \times c/b$, in which "c" is the amount of alkanes in the product and "b" is as defined hereinbefore.

Comparison of the results of Examples 1, 2 and 3 shows that the presence of at least 5 equivalents of the acid per gram atom of palladium enhances 1-octene conversion.

Examples 6 to 11 show that the isomer mixture of 1-, 2-, 3- and 4-octenes is easily hydroformylated in a variety of aprotic solvents, producing nonanals of high linearity; the highest conversion was obtained in Example 9 with methyl benzoate.

Comparative Experiments A and B show that the presence of monodentate ligands has no significant catalytic action.

Comparative Experiments C and E show that the presence of acetic acid or p-toluenesulfonic acid, respectively, has no catalytic action and Comparative Experiment D shown that the presence of benzenephosphonic acid has only little catalytic action.

Comparative Experiment F shows that the presence of ruthenium acetylacetonate has little catalytic action.

Comparative Experiment G shows that 1,2-di(diphenylphosphino)-ethane has only little catalytic action.

TABLE I

| Example | Comparative Experiment | Catalytic System (mmol) | | | Octene ml | Temp. °C. | Solvent ml | Time h |
|---|---|---|---|---|---|---|---|---|
| 1 | | Pd acetate (0.1) | $p_2P(CH_2)_3Pp_2(0.3)$ | $CF_3COOH(2)$ | 1-octene(10) | 100 | diglyme | 5 |
| | A | " | $Pp_3(3)$ | $CF_3COOH(4)$ | " | 135 | " | " |
| | B | " | $Pp_3(0.5)$ | $CF_3COOH(1)$ | " | 125 | " | " |
| 2 | | " | $p_2P(CH_2)_3Pp_2(0.3)$ | $CF_3COOH(1)$ | 20 | 125 | " | " |
| 3 | | " | $p_2P(CH_2)_3Pp_2(0.3)$ | $CF_3COOH(0.5)$ | " | " | " | " |
| 4 | | " | $p_2P(CH_2)_3Pp_2(0.3)$ | $CF_3COOH(2)$ | " | " | toluene | " |
| | C | " | $p_2P(CH_2)_3Pp_2(0.3)$ | $CH_3COOH(4)$ | " | " | diglyme | " |
| | D | " | $p_2P(CH_2)_3Pp_2(0.3)$ | $H_2PO_3p(1)$ | " | " | toluene | " |
| | E | " | $p_2P(CH_2)_3Pp_2(0.3)$ | PTsA(2) | " | " | " | " |
| 5 | | Pt(Acac)$_2$(0.1) | $p_2P(CH_2)_3Pp_2(0.3)$ | $CF_3COOH(2)$ | " | " | " | " |
| | F | Ru(Acac)$_3$(0.1) | $p_2P(CH_2)_4Pp_2(0.3)$ | $CF_3COOH(1)$ | " | " | " | " |
| 6 | | Pd acetate(0.4) | $p_2P(CH_2)_4Pp_2(1.2)$ | $CF_3COOH(4)$ | i-octenes(20) | 155 | " | " |
| 7 | | Pd acetate(0.4) | $p_2P(CH_2)_4Pp_2(1.2)$ | $CF_3COOH(4)$ | " | 125 | anisole | 10 |
| 8 | | Pd acetate(0.4) | $p_2P(CH_2)_4Pp_2(1.2)$ | $CF_3COOH(4)$ | " | " | diphenyl ether | 10 |
| 9 | | | $p_2P(CH_2)_4Pp_2(1.2)$ | $CF_3COOH(4)$ | " | 145 | methyl benzoate | 10 |
| 10 | | Pd acetate(0.4) | $p_2P(CH_2)_4Pp_2(1.2)$ | $CF_3COOH(8)$ | " | 125 | anisole | 10 |

TABLE I-continued

| Example | Comparative Experiment | Catalytic System (mmol) | | | Octene ml | Temp. °C. | Solvent ml | Time h |
|---|---|---|---|---|---|---|---|---|
| 11 |  | Pd acetate(0.4) | $\phi_2P(CH_2)_4P\phi_2$(1.2) | $CF_3COOH$(4) | " | " | o-dichlorobenzene | 10 |
|  | G | Pd acetate(0.1) | $\phi_2P(CH_2)_2P\phi_2$(0.3) | $CF_3COOH$(2) | 1-octene(10) | 110 | diglyme | 5 |

TABLE II

| Example or Comparative Experiment | Octene Conversion % | Selectivity To Nonanals % | Linearity Of Nonanals % | Selectivity To Alkanes % |
|---|---|---|---|---|
| 1 | 41 | 100 | 71.9 | 0 |
| A | 0 | — | — | — |
| B | 0 | — | — | — |
| 2 | 39.7 | 100 | 72.6 | 0 |
| 3 | 17.1 | 100 | 83.2 | 0 |
| 4 | 30.2 | 93.0 | 69.9 | <2 |
| C | 0 | — | — | — |
| D | 14 | 100 | 62.4 | 0 |
| E | 0 | — | — | — |
| 5 | 23 | 96 | 64.3 | 1.6 |
| F | 4 | 95 | 64.6 | <1 |
| 6 | 30 | 88.2 | 69.0 | 5.9 |
| 7 | 64 | 91.4 | 66.7 | 1.3 |
| 8 | 58 | 97 | 66.5 | 1.5 |
| 9 | 67 | 85 | 65.9 | 2.6 |
| 10 | 64 | 73 | 67.9 | 2.8 |
| 11 | 59 | 87 | 72.3 | 4.0 |
| G | 5 | 100 | 64.1 | 0 |

I claim as my invention:

1. A process for the preparation of aldehydes by hydroformylation of an alkenically unsaturated compound having at least 5 carbon atoms per molecule, which comprises contacting the alkenically unsaturated compound with carbon monoxide, in a molar ratio of carbon monoxide to unsaturated compound in the range from 5:95 to 95:5, and hydrogen, in a molar ratio of hydrogen to carbon monoxide between about 12:1 and 1:12, at a temperature between about 20° and 200° C. and at a pressure between about 1 and 100 bar in the presence of an aprotic solvent and a catalytic system comprising (a) one or more catalysts selected from the group consisting of palladium, palladium compounds, platinum and platinum compounds, in a quantity in the range from $10^{-8}$ to $10^{-1}$ mol of catalyst per mol of alkenically unsaturated compound, (b) one or more anions of one or more carboxylic acids having a pKa<2, measured in aqueous solution at 18° C., in a quantity of at least 5 equivalents of carboxylic acid anions per gram atom of palladium and platinum, and (c) one or more bidentate ligands of the formula

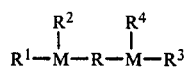

wherein M represents phosphorus, arsenic or antimony, R represents a divalent organic bridging group having at least three carbon atoms in the bridge, and $R^1$, $R^2$, $R^3$ and $R^4$ are the same or different hydrocarbon groups, in a quantity of 0.1 to 10 mols of bidentate ligand per mol of palladium, palladium compound, platinum and platinum compound.

2. The process of claim 1, in which the carboxylic acid is trifluoroacetic acid.

3. The process of claim 2, in which the hydrocarbon groups $R^1$, $R^2$, $R^3$ and $R^4$ are aryl groups containing 6–14 carbon atoms.

4. The process of claim 3, in which the aryl groups are phenyl groups.

5. The process of claim 4, in which the component (a) is one or more palladium compounds.

6. The process of claim 5, in which the bidentate ligand is a phosphine.

7. The process of claim 6, in which R represents a trimethylene group.

8. The process of claim 7, in which the ligand is 1,3-di(diphenylphosphino)propane or 1,4-di(diphenylphosphino)butane.

9. The process of claim 8, in which the alkenically unsaturated hydrocarbon is an alkene.

10. A process for the preparation of aldehydes by hydroformylation of an alkenically unsaturated compound having at least 5 carbon atoms per molecule, which comprises contacting the alkenically unsaturated starting material having a linear structure in a major portion of the molecules with carbon monoxide, in a molar ratio of carbon monoxide to unsaturated compound in the range from 5:95 to 95:5, and hydrogen, in a molar ratio of hydrogen to carbon monoxide between about 12:1 and 1:12, at a temperature between about 20° and 200° C. and at a pressure between about 1 and 100 bar in the presence of an aprotic solvent and a catalytic system comprising (a) one or more catalysts selected from the group consisting of palladium, palladium compounds, platinum and platinum compounds, in a quantity in the range from $10^{-8}$ to $10^{-1}$ mol of catalyst per mol of alkenically unsaturated compound, (b) one or more anions of one or more carboxylic acids having a pKa<2, measured in aqueous solution at 18° C., in a quantity of at least 5 equivalents of carboxylic acid anions per gram atom of palladium and platinum, and (c) one or more bidentate ligands of the formula

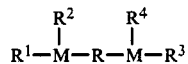

wherein M represents phosphorus, arsenic or antimony, R represents a divalent organic bridging group having at least three carbon atoms in the bridge, and $R^1$, $R^2$, $R^3$ and $R^4$ are the same or different hydrocarbon groups, in a quantity of 0.1 to 10 mols of bidentate ligand per mol of palladium, palladium compound, platinum and platinum compound.

11. The process of claim 10, in which the carboxylic acid is trifluoroacetic acid.

12. The process of claim 11, in which the hydrocarbon groups $R^1$, $R^2$, $R^3$ and $R^4$ are aryl groups containing 6–14 carbon atoms.

13. The process of claim 12, in which the aryl groups are phenyl groups.

14. The process of claim 13, in which the component (a) is one or more palladium compounds.

15. The process of claim 14, in which the bidentate ligand is a phosphine.

16. The process of claim 15, in which R represents a trimethylene group, the ligand is 1,3-di(diphenylphosphino)propane or 1,4-di(diphenylphosphino)butane, and the alkenically unsaturated hydrocarbon is an alkene.

* * * * *